United States Patent [19]
Drake et al.

[11] Patent Number: 4,662,879
[45] Date of Patent: May 5, 1987

[54] RUMEN BOLUS

[75] Inventors: Cyril F. Drake, Harlow; Mary Tripp, Bishop's Stortford, both of England

[73] Assignee: STC plc, London, England

[21] Appl. No.: 775,662

[22] Filed: Sep. 13, 1985

[30] Foreign Application Priority Data

Sep. 15, 1984 [GB] United Kingdom ............... 8423386

[51] Int. Cl.$^4$ .............................................. A61K 9/26
[52] U.S. Cl. ..................................... 604/892; 424/438; 604/93
[58] Field of Search .................. 604/93, 890–892; 424/14–16, 22, 24

[56] References Cited

U.S. PATENT DOCUMENTS 3,760,806  9/1973  Leeper ................................ 604/892
4,055,178 10/1977  Harrigan ............................ 604/892
4,381,780  5/1983  Holloway ........................... 604/892
4,407,786 10/1983  Drake et al. .................... 604/93 X
4,449,981  5/1984  Drake et al. ...................... 604/890

FOREIGN PATENT DOCUMENTS 2125698  3/1984  United Kingdom ................. 604/93

Primary Examiner—Dalton L. Truluck
Attorney, Agent, or Firm—Kerkam, Stowell, Kondracki & Clarke

[57] ABSTRACT

A rumen bolus for supplying a mineral supplement to a ruminant animal comprises a water soluble glass incorporating the mineral and contained in an apertured insert, e.g. plastics, housing. Typically the glass is in the form of tubes or pellets so as to provide a substantially constant dissolution rate.

11 Claims, 1 Drawing Figure

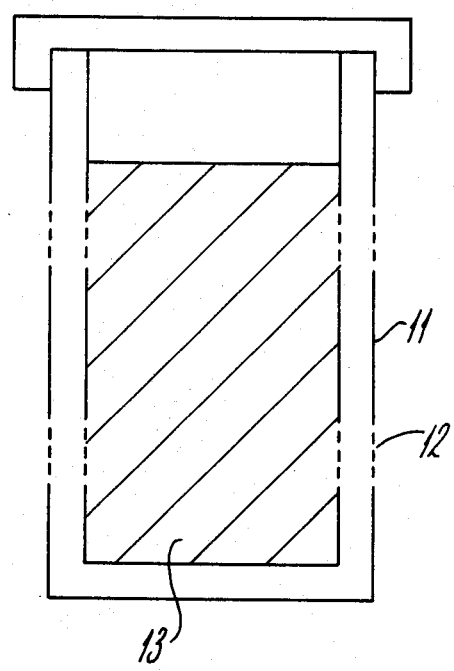

RUMEN BOLUS

This invention relates to the intraruminal delivery of mineral supplement to ruminant animals and to a rumen bolus for such delivery.

It has been found that the delivery of mineral supplements to ruminant animals, e.g. sheep and cattle, results in increased growth rate and improved health of the animals. It has been proposed to provide such a mineral supplement from a soluble bolus, e.g. of a water soluble glass, which lodges in the rumen of the animals and slowly dissolves to release the minerals. The surface area of such a device reduces with time and thus the release rate of the mineral also decreases. Further the casting and annealing operations involved in the manufacture of a large bolus are time consuming and thus result in a relatively high manufacturing cost.

The object of the invention is to minimise or to overcome these disadvantages.

According to the invention there is provided a rumen bolus for the delivery of a mineral supplement to an animal, said bolus including an insoluble housing having a plurality of openings, through which, in use, the intestinal fluids of the animal penetrate into the interior of the housing, and wherein said housing contains one or more bodies formed from a water soluble glass incorporating the mineral supplement.

An embodiment of the invention will now be described with reference to the accompanying drawing in which the single FIGURE is a vertical view of the rumen bolus.

Referring to the drawing, the bolus comprises a housing 11, e.g. of a plastics material, having a plurality of openings 12. Typically the housing comprises a plastics mesh, but it may also comprise a rigid container provided e.g. with a snap-on lid. The housing 11 contains one or more bodies 13 each comprising a water soluble glass incorporating a mineral supplement. The bodies 13 may comprise granules, or, advantageously, platelets or tubes. The latter two forms are to be preferred as their surface configuration provides a substantially constant dissolution rate. Where platelets are employed these are typically 5 to 10 mm in diameter and 1 to 3 mm in thickness.

The glass contains the mineral to be released e.g. in the form of an oxide. Typically the glass incorporates copper as a mineral supplement. Other minerals include, but are in no way limited to, iron, zinc, cobalt, magnesium, selenium and iodine as mineral supplements. Advantageously the bolus contains a plurality of glass compositions in pellet form, the mix being predetermined, e.g. by veterinary diagnosis, for the particular animal to which the bolus is to be administered. Compositions of differing dissolution rates may also be employed to provide variation in the composition of released minerals over an extend period.

A number of water soluble glasses may be used for this purpose. Typical of such compositions are those described in our published specification Nos. 2030559, 2037735 and 2081703. The technique is not of course limited to these compositions. Furthermore one or more organic materials may also be incorporated in the bolus e.g. to provide for the release of an anthelmintic or of an antibiotic. The bolus may also incorporate glass/polymer composite structures such as are described in our published specification No. 2 111 388.

A typical glass for supplying copper comprises
28.2 mole % CuO
25.0 mole % $Na_2O$
41.8 mole % $P_2O_5$
5.0 mole % ZnO
This is equivalent to 17.6 wt % copper.

This glass was prepared by melting the following constituents for one and a half hours at 1100° C. in an oxidising atmosphere:
$Cu_2P_2O_7 3H_2O$: 601 g
$Zn_3(PO_4)_2 2H_2O$: 85.5 g
Na H $PO_4$: 715.5 g
$P_2O_5$: 30 g The weight loss during melting was 200 g.

The melt was cast on to a chilled steel plate, crushed and then smelted at 1050° C. This melt was cast into a pellet mould and annealed from 335° C. to ambient temperature over a period of 15 hrs. The pellets thus produced had a diameter of 11 mm and a thickness of 2.8 mm. The in vitro dissolution rate measured in deionised water at 38° C. was 1.58 mg Cu/pellet/day which is equivalent to 0.6 mg $Cu/cm^2$/day. Such a dissolution rate is appropriate for the supply of copper to a ruminant animal.

It will be appreciated by those skilled in the art that, because of the unpredictable manner in which some metal oxides and certain oxide combinations can effect glass dissolution rates, it may be difficult or impractical to provide a conventional solid glass bolus that will release a plurality of minerals each at the optimum rate for animal therapy. This disadvantage of a conventional bolus can be overcome using the techniques described herein by providing, in a single bolus construction, a plurality of glass compositions each designed to release a particular element or elements at a rate corresponding to the nutritional requirements of an animal to which the bolus is administered.

We claim:

1. A rumen bolus for the simultaneous delivery of a plurality of mineral supplement to a ruminant animal, the bolus including an insoluble housing having a plurality of openings through which, in use, the intestinal fluids of the animal penetrate into the interior of the housing, and a plurality of water soluble bodies, at least one for each said mineral supplement, contained in said housing and each consisting essentially of a water soluble glass, and wherein each said glass body incorporates the corresponding mineral supplement as an oxide constituent of the glass.

2. A bolus as claimed in claim 1, wherein the glass bodies are in the form of platelets.

3. A bolus as claimed in claim 2, wherein said platelets are 5 to 10 mm in diameter and 1 to 3 mm in thickness.

4. A bolus as claimed in claim 1, wherein the glass bodies are in tubular form.

5. A bolus as claimed in claim 2, wherein said glass contains copper.

6. A bolus as claimed in claim 3, wherein said glass contains a mineral supplement selected for the group consisting of selenium, iron, cobalt, zinc, iodine, magnesium and mixtures thereof.

7. A bolus as claimed in claim 1, and further including an organic material.

8. A bolus as claimed in claim 7, wherein said organic material comprises an anthelmintic.

9. A bolus as claimed in claim 1, wherein each said water soluble body comprises a glass/polymer composite.

10. A bolus as claimed in claim 1, wherein said housing comprises a plastics mesh.

11. A bolus as claimed in claim 1, wherein said housing comprises a rigid body with a snap-on lid.

* * * * *

UNITED STATES PATENT AND TRADEMARK OFFICE
CERTIFICATE OF CORRECTION

PATENT NO. : 4,662,879

DATED : May 5, 1987

INVENTOR(S) : Drake et al

It is certified that error appears in the above-identified patent and that said Letters Patent is hereby corrected as shown below:

Column 2, Line 35, delete "supplement" add --supplements--.
Column 2, Line 54, "claim 3" should be --claim 2--.

Signed and Sealed this

Twentieth Day of October, 1987

Attest:

DONALD J. QUIGG

Attesting Officer

Commissioner of Patents and Trademarks